United States Patent
Nishimori et al.

(10) Patent No.: US 10,065,940 B2
(45) Date of Patent: Sep. 4, 2018

(54) EPISULFIDE COMPOUND AND OPTICAL MATERIAL COMPOSITION CONTAINING SAME

(71) Applicant: MITSUBISHI GAS CHEMICAL COMPANY, INC., Tokyo (JP)

(72) Inventors: Yoshihiko Nishimori, Tokyo (JP); Teruo Kamura, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/521,723

(22) PCT Filed: Mar. 1, 2016

(86) PCT No.: PCT/JP2016/056154
§ 371 (c)(1),
(2) Date: Apr. 25, 2017

(87) PCT Pub. No.: WO2016/158157
PCT Pub. Date: Oct. 6, 2016

(65) Prior Publication Data
US 2017/0247351 A1 Aug. 31, 2017

(30) Foreign Application Priority Data
Mar. 31, 2015 (JP) ................. 2015-072688

(51) Int. Cl.
| C07D 331/02 | (2006.01) |
| C08G 18/76 | (2006.01) |
| G02B 1/04 | (2006.01) |
| C08G 18/38 | (2006.01) |
| C08G 18/32 | (2006.01) |
| G02C 7/00 | (2006.01) |
| C08G 75/08 | (2006.01) |

(52) U.S. Cl.
CPC ....... *C07D 331/02* (2013.01); *C08G 18/3203* (2013.01); *C08G 18/3874* (2013.01); *C08G 18/7614* (2013.01); *C08G 75/08* (2013.01); *G02B 1/04* (2013.01); *G02B 1/041* (2013.01); *G02C 7/00* (2013.01)

(58) Field of Classification Search
CPC .............. C07D 331/02; C08G 18/3203; C08G 18/3874; C08G 18/7614; C08G 75/08; G02B 1/041; G02B 1/04; G02C 7/00
See application file for complete search history.

(56) References Cited

U.S. PATENT DOCUMENTS

| 6,117,923 A | 9/2000 | Amagai et al. |
| 6,472,495 B1 | 10/2002 | Yoshimura et al. |
| 2003/0171533 A1 | 9/2003 | Tamura et al. |
| 2003/0195270 A1 | 10/2003 | Ishii et al. |
| 2004/0122201 A1 | 6/2004 | Yoshimura et al. |
| 2005/0154073 A1 | 7/2005 | Ishii et al. |
| 2005/0261467 A1 | 11/2005 | Tamura et al. |
| 2009/0018308 A1* | 1/2009 | Kamura ............ C08G 75/08 528/375 |
| 2010/0331515 A1 | 12/2010 | Takeuchi et al. |
| 2014/0371475 A1 | 12/2014 | Aoki et al. |

FOREIGN PATENT DOCUMENTS

| CN | 101630210 | 1/2010 |
| JP | 9-110979 | 4/1997 |
| JP | 10-298287 | 11/1998 |
| JP | 2001-002783 | 1/2001 |
| JP | 2001-131257 | 5/2001 |
| JP | 2001-163875 A * | 6/2001 |
| JP | 2002-122701 | 4/2002 |

(Continued)

OTHER PUBLICATIONS

International Search Report issued in WIPO Patent Application No. PCT/JP2016/056154, dated May 31, 2016.

*Primary Examiner* — Rabon A Sergent

(74) *Attorney, Agent, or Firm* — Greenblum & Bernstein, P.L.C.

(57) ABSTRACT

According to the present invention, it is possible to provide an optical material composition that contains an episulfide compound represented by formula (1) and an episulfide compound represented by formula (2). According to this optical material composition, it is possible to suppress a reduction in the yield rate caused by molding defects, and possible to obtain an optical material having excellent dyeability.

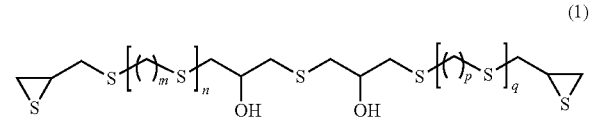

(1)

(In formula (1), m and p are each an integer between 0 and 4, and n and q are each an integer between 0 and 2.)

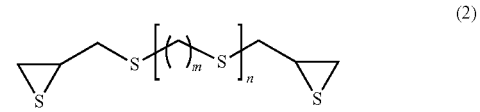

(2)

(In formula (2), m is an integer between 0 and 4 and n is an integer between 0 and 2).

12 Claims, No Drawings

(56) References Cited

FOREIGN PATENT DOCUMENTS

| | | | |
|---|---|---|---|
| JP | 2003-119286 A | * | 4/2003 |
| JP | 2003-226718 | | 8/2003 |
| JP | 2004-27203 | | 1/2004 |
| JP | 2005-272418 | | 10/2005 |
| KR | 10-2009-0088240 | | 8/2009 |
| WO | 02/083763 | | 10/2002 |
| WO | 2009/101867 | | 8/2009 |
| WO | 2013/157490 | | 10/2013 |
| WO | 2014142138 A1 | | 9/2014 |

* cited by examiner

EPISULFIDE COMPOUND AND OPTICAL MATERIAL COMPOSITION CONTAINING SAME

TECHNICAL FIELD

The present invention relates to a novel episulfide compound and a composition for optical materials containing the same, and particularly relates to a novel episulfide compound, which is suitably used for an optical material for a plastic lens, a prism, an optical fiber, an information recording substrate, a filter or the like, in particular for a plastic lens, and a composition for optical materials containing the same.

BACKGROUND ART

Plastic lenses are lightweight, highly tough and easy to be dyed. Properties particularly required for plastic lenses are: low specific gravity; high transparency; low yellowness; high refractive index and high Abbe number as optical properties; high heat resistance; high strength; and the like. A high refractive index allows a lens to be thinner, and a high Abbe number reduces the chromatic aberration of a lens.

Recently, many examples using an organic compound having a sulfur atom for providing a high refractive index and a high Abbe number have been reported. Among such examples, polyepisulfide compounds having a sulfur atom are known to provide a good balance between the refractive index and the Abbe number (Patent Document 1). Further, since polyepisulfide compounds can be reacted with various compounds, for the purpose of the improvement of physical properties, compositions in combination with various compounds have been proposed (Patent Documents 2-5).

However, there is a case where it is difficult to dye a lens produced from an episulfide compound according to a method generally used for plastic lenses, and sometimes required characteristics of spectacle lenses in which importance is placed on design property are not sufficiently achieved. Further, in the case of powerful lenses, there is a case where a lens is broken at the time of demolding due to poor mold release characteristics, or there is a case where required surface accuracy cannot be obtained because a lens is released from a mold during polymerization due to excessively high mold release characteristics.

PRIOR ART DOCUMENTS

Patent Documents

Patent Document 1: Japanese Laid-Open Patent Publication No. H09-110979
Patent Document 2: Japanese Laid-Open Patent Publication No. H10-298287
Patent Document 3: Japanese Laid-Open Patent Publication No. 2001-002783
Patent Document 4: Japanese Laid-Open Patent Publication No. 2001-131257
Patent Document 5: Japanese Laid-Open Patent Publication No. 2002-122701

SUMMARY OF THE INVENTION

Problems to be Solved by the Invention

The problem to be solved by the present invention is to provide a composition for optical materials, which can suppress reduction in the yield rate caused by mold release failure, and an optical material having excellent dyeability.

Means for Solving the Problems

Under such circumstances, the present inventors diligently made researches and solved the problem by using an episulfide compound represented by formula (1) below and a composition for optical materials which contains the episulfide compound represented by formula (1) below and an episulfide compound represented by formula (2) below, and thus the present invention was achieved. Specifically, the present invention is as follows:

<1> An episulfide compound represented by formula (1):

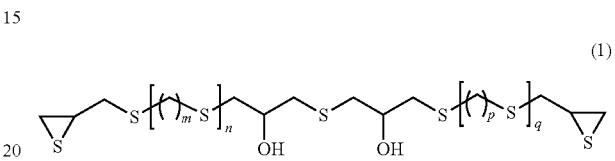

wherein m and p are each an integer between 0 and 4 and n and q are each an integer between 0 and 2.

<2> A composition for optical materials, which contains the episulfide compound represented by formula (1) according to item <1> and an episulfide compound represented by formula (2):

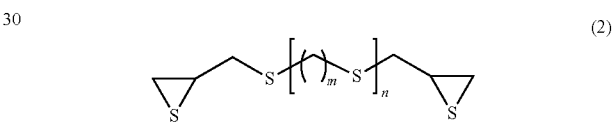

wherein m is an integer between 0 and 4 and n is an integer between 0 and 2.

<3> The composition for optical materials according to item <2>, wherein the content of the episulfide compound represented by formula (1) is 0.001 to 5.0% by mass.

<4> The composition for optical materials according to item <2> or <3>, wherein the content of the episulfide compound represented by formula (2) is 40 to 99.999% by mass.

<5> The composition for optical materials according to any one of items <2> to <4>, further containing polythiol.

<6> The composition for optical materials according to any one of items <2> to <5>, further containing sulfur.

<7> The composition for optical materials according to item <5> or <6>, further containing polyisocyanate.

<8> A polymerizable and curable composition, which contains the composition for optical materials according to any one of items <2> to <7> and a polymerization catalyst in an amount of 0.0001 to 10% by mass relative to the total amount of the composition for optical materials.

<9> An optical material obtained by curing the composition for optical materials according to any one of items <2> to <7> or the polymerizable and curable composition according to item <8>.

<10> An optical lens comprising the optical material according to item <9>.

<11> A method for producing an optical material, which comprises a step of adding a polymerization catalyst in an amount of 0.0001 to 10% by mass relative to the total amount of the composition for optical materials according to any one of items <2> to <7> to be polymerized and cured.

<12> The method for producing an optical material according to item <11>, wherein the episulfide compound represented by formula (2) and sulfur are partially subjected to a polymerization reaction in advance, followed by polymerization and curing.

Advantageous Effect of the Invention

According to the present invention, it is possible to obtain a composition for optical materials, by which mold release failure is not easily caused in the production of an optical material having a high refractive index, and by which an optical material having excellent dyeability can be obtained.

Embodiments For Carrying Out The Invention

Hereinafter, the present invention will be described in detail.

The present invention relates to an episulfide compound represented by formula (1) above, and a composition for optical materials containing the episulfide compound represented by formula (1) above and a polymerizable compound. Examples of the polymerizable compound include an episulfide compound, a vinyl compound, a methacrylic compound, an acrylic compound and an allyl compound. Among them, an episulfide compound is preferred, and an episulfide compound represented by formula (2) above is more preferred.

The ratio of the episulfide compound represented by formula (1) above in the composition for optical materials of the present invention is preferably 0.001 to 5.0% by mass, more preferably 0.005 to 3.0% by mass, and particularly preferably 0.01 to 1.0% by mass. When the ratio of the episulfide compound represented by formula (1) is less than 0.001% by mass, sufficient effects may not be obtained. When the ratio is more than 5.0% by mass, mold release characteristics may be deteriorated. Further, the ratio of the polymerizable compound in the composition for optical materials of the present invention is preferably 95.0 to 99.999% by mass, more preferably 97.0 to 99.995% by mass, and particularly preferably 99.0 to 99.99% by mass. When using the episulfide compound represented by formula (2) above as the polymerizable compound, the ratio of the episulfide compound represented by formula (2) above in the composition for optical materials is preferably 40 to 99.999% by mass, more preferably 50 to 99.995% by mass, and particularly preferably 60 to 99.99% by mass.

Hereinafter, the episulfide compound represented by formula (1) above and the episulfide compound represented by formula (2) above will be described in detail.

The present invention relates to the episulfide compound represented by formula (1) above, and the episulfide compound represented by formula (1) is used in the composition for optical materials of the present invention. In formula (1), it is preferred that m and p are each an integer between 0 and 2 and that n and q are each an integer of 0 or 1. More preferred is a compound in which m and p are 0 and n and q are 1 or a compound in which n and q are 0, and most preferred is a compound in which n and q are 0. As the episulfide compound represented by formula (1), such compounds may be used solely, or two or more of them may be used in combination.

Hereinafter, the method for producing the episulfide compound represented by formula (1) of the present invention will be described, but the production method is not limited thereto.

In the method for producing the episulfide compound represented by formula (1) of the present invention, firstly hydrogen sulfide or polythiol is reacted with an epihalohydrin compound to obtain a compound represented by formula (3) below. In the case of obtaining a compound in which n and q are 0 or a compound in which m and p are 0 and n and q are 1, subsequently the obtained compound represented by formula (3) is reacted with a thialation agent such as thiourea and a thiocyanate to obtain a compound represented by formula (4). In the case of producing the compound in which n and q are 0, the compound represented by formula (4) is reacted with an epihalohydrin compound to obtain a compound represented by formula (5) below, subsequently the obtained compound represented by formula (5) is reacted with an alkali to promote a dehydrohalogenation reaction, thereby obtaining a compound represented by formula (6) below, and then the obtained compound represented by formula (6) is reacted with a thialation agent such as thiourea and a thiocyanate, thereby obtaining the episulfide compound represented by formula (1).

In the case of producing the compound in which m and p are 0 and n and q are 1, the compound represented by formula (4) is reacted with 3-mercapto-1,2-propylenesulfide, thereby obtaining the episulfide compound represented by formula (1). In another production method, the compound represented by formula (3) is reacted with an alkali to promote a dehydrohalogenation reaction, thereby obtaining a compound represented by formula (7) below, and after that, it is reacted with hydrogen sulfide to obtain a compound represented by formula (8) below, and then the obtained compound represented by formula (8) is reacted with a thialation agent such as thiourea and a thiocyanate, thereby obtaining the episulfide compound represented by formula (1).

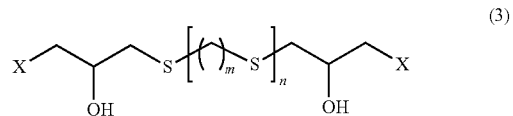

(3)

(In the formula, X represents a halogen atom, m represents an integer between 0 and 4, and n represents an integer between 0 and 2.)

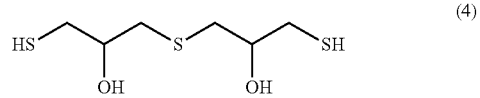

(4)

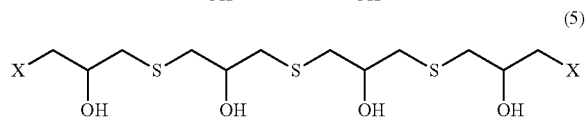

(5)

(In the formula, X represents a halogen atom.)

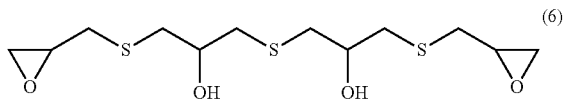

(6)

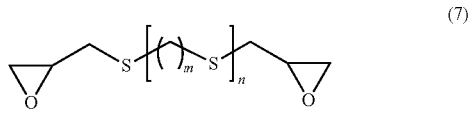

(7)

(In the formula, m represents an integer between 0 and 4, and n represents an integer between 0 and 2.)

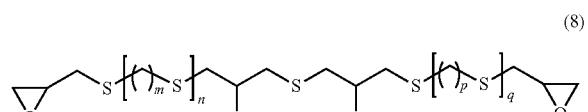

(8)

(In the formula, m and p represent an integer between 0 and 4, and n and q represent an integer between 0 and 2.)

The method for producing the compound represented by formula (3) will be described below. By using the compound represented by formula (7) instead of the epihalohydrin compound, the compound represented by formula (8) can be produced in the same manner.

The compound represented by formula (3) can be obtained by reacting hydrogen sulfide or a polythiol compound with the epihalohydrin compound. Examples of the polythiol compound include methanedithiol, 1,2-dimercaptoethane, 1,3-dimercaptopropane, 1,4-dimercaptobutane and bis(2-mercaptoethyl)sulfide. Among hydrogen sulfide and polythiol compounds, hydrogen sulfide, 1,2-dimercaptoethane and bis(2-mercaptoethyl)sulfide are preferred, and hydrogen sulfide is most preferred. Examples of the epihalohydrin compound include epichlorohydrin and epibromohydrin, and preferred is epichlorohydrin.

When reacting epihalohydrin with hydrogen sulfide or the polythiol compound, a catalyst is preferably used. Examples of the catalyst include inorganic acids, organic acids, Lewis acids, silicic acid, boric acid, quaternary ammonium salts, inorganic bases and organic bases. Among them, organic acids, quaternary ammonium salts and inorganic bases are preferred, and quaternary ammonium salts and inorganic bases are more preferred. Specific examples thereof include tetramethylammonium chloride, tetramethylammonium bromide, tetramethylammonium acetate, tetraethylammonium chloride, tetraethylammonium bromide, tetraethylammonium acetate, tetrabutylammonium chloride, tetrabutylammonium bromide, tetrabutylammonium acetate, tetrahexylammonium chloride, tetrahexylammonium bromide, tetrahexylammonium acetate, tetraoctylammonium chloride, tetraoctylammonium bromide, tetraoctylammonium acetate, sodium hydroxide, potassium hydroxide, magnesium hydroxide and calcium hydroxide. Among them, sodium hydroxide, potassium hydroxide and calcium hydroxide are preferred.

The amount of the catalyst to be added is not particularly limited as long as it is for promoting a reaction, but is preferably 0.00001 to 0.5 mol, and more preferably 0.001 to 0.1 mol per 1 mol of epihalohydrin. When the amount is less than 0.00001 mol, the reaction does not proceed or is too slow, and it is undesirable. When the amount is more than 0.5 mol, the reaction proceeds excessively and is difficult to be controlled, and it is undesirable.

The ratio between epihalohydrin and hydrogen sulfide or the polythiol compound is not particularly limited as long as the reaction proceeds, but the molar ratio of epihalohydrin to the thiol group (SH group) of the polythiol compound or H of hydrogen sulfide is preferably 0.3 to 4, more preferably 0.4 to 3, and even more preferably 0.5 to 2. When the molar ratio is less than 0.3 or more than 4, the amount of unreacted raw materials increases, and it is undesirable from the economical viewpoint.

A solvent may be used but does not have to be used. In the case of using the solvent, water, alcohols, ethers, ketones, aromatic hydrocarbons, halogenated hydrocarbons, etc. can be used. Specific examples thereof include water, methanol, ethanol, propanol, isopropanol, diethyl ether, tetrahydrofuran, dioxane, methyl cellosolve, ethyl cellosolve, butyl cellosolve, methyl ethyl ketone, acetone, benzene, toluene, xylene, dichloroethane, chloroform and chlorobenzene. Among them, water, methanol and toluene are preferred, and water and methanol are particularly preferred.

The reaction temperature is not particularly limited as long as it is for promoting a reaction, but is preferably $-10°$ C. to $80°$ C., more preferably $0°$ C. to $50°$ C., and even more preferably $0°$ C. to $40°$ C. The reaction time is not particularly limited, but is usually 20 hours or less. When the reaction temperature is lower than $-10°$ C., the reaction does not proceed or is too slow, and it is undesirable. When the reaction temperature is higher than $80°$ C., oligomerization occurs, resulting in a high molecular weight, and it is undesirable.

The method for producing the compound represented by formula (4) from the compound represented by formula (3) will be described below.

The compound represented by formula (4) is obtained by reacting the compound represented by formula (3) with a thialation agent such as thiourea and a thiocyanate. Preferred thialation agents are thiourea, sodium thiocyanate, potassium thiocyanate and ammonium thiocyanate, and particularly preferred is thiourea. The thialation agent is used in a mole number corresponding to halogen of the compound represented by formula (3), i.e., a theoretical amount, but when importance is placed on the reaction rate and the purity, the thialation agent is used in the theoretical amount to 2.5 times the theoretical amount (mol). The amount is preferably from 1.3 times the theoretical amount (mol) to 2.0 times the theoretical amount (mol), and more preferably from 1.5 times the theoretical amount (mol) to 2.0 times the theoretical amount (mol).

The solvent is not particularly limited as long as it dissolves the thialation agent, the compound represented by formula (4) and the compound represented by formula (3). Specific examples thereof include: alcohols such as methanol and ethanol; ethers such as diethyl ether, tetrahydrofuran and dioxane; hydroxy ethers such as methyl cellosolve, ethyl cellosolve and butyl cellosolve; aromatic hydrocarbons such as benzene and toluene; halogenated hydrocarbons such as dichloromethane, chloroform and chlorobenzene; and water. Preferred are alcohols, aromatic hydrocarbons and water, and more preferred are methanol and toluene. These substances may be used solely, or two or more of them may be used in combination.

The reaction temperature is not particularly limited as long as the reaction proceeds, but the reaction is usually performed at $10°$ C. to $50°$ C. When the reaction temperature is lower than $10°$ C., not only the reaction rate is reduced, but also the thialation agent is not sufficiently dissolved and the reaction does not proceed sufficiently, and when the temperature is higher than $50°$ C., polymer formation becomes pronounced.

It is preferred to add an acid, acid anhydride or ammonium salt at the time of the reaction. Specific examples of the acid or acid anhydride to be used include: inorganic acidic compounds such as nitric acid, hydrochloric acid, perchloric acid, hypochlorous acid, chlorine dioxide, hydrofluoric acid, sulfuric acid, fuming sulfuric acid, sulfuryl chloride, boric acid, arsenic acid, arsenious acid, pyroarsenic acid, phosphoric acid, phosphorous acid, hypophosphoric acid, phosphorus oxychloride, phosphorous oxybromide, phosphorus sulfide, phosphorus trichloride, phosphorus tribromide, phosphorus pentachloride, hydrocyanic acid, chromic acid, nitric anhydride, sulphuric anhydride, boron oxide, arsenic pentoxide, phosphorus pentoxide, chromic anhydride, silica gel, silica alumina, aluminium chloride and zinc chloride; organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid, acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride; phosphoric acids such as mono-, di- or trimethyl phosphate, mono-, di- or triethyl phosphate, mono-, di- or triisobutyl phosphate, mono-, di- or tributyl phosphate and mono-, di- or trilauryl phosphate, and phosphorous acids in which the phosphate moiety of any of the phosphoric acids is changed to a phosphite; organic phosphorous compounds such as dialkyl phosphorodithioates typified by dimethyl phosphorodithioate; phenols such as phenol, catechol, t-butyl catechol, 2,6-di-t-butyl cresol, 2,6-di-t-butyl ethylphenol, resorcin, hydroquinone, phloroglucin, pyrogallol, cresol, ethyl phenol, butyl phenol, nonyl phenol, hydroxyphenylacetic acid, hydroxyphenylpropionic acid, hydroxyphenylacetamide, methyl hydroxyphenylacetate, ethyl hydroxyphenylacetate, hydroxyphenethyl alcohol, hydroxyphenethyl amine, hydroxybenzaldehyde, phenylphenol, bisphenol A, 2,2'-methylene-bis(4-methyl-6-t-butyl phenol), bisphenol F, bisphenol S, α-naphthol, β-naphthol, aminophenol, chlorophenol and 2,4,6-trichlorophenol; and sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulfanilic acid, 4B-acid, diaminostilbenesulfonic acid, biphenylsulfonic acid, α-naphthalenesulfonic acid, β-naphthalenesulfonic acid, peri acid, Laurent's acid and phenyl-J-acid. Several of them may be used in combination. Preferred are organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid, acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. More preferred are acid anhydrides such as acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. Acetic anhydride is most preferred. The amount to be added is usually 0.001 to 10% by mass, and preferably 0.01 to 5% by mass relative to the total amount of the reaction solution. When the amount to be added is less than 0.001% by mass, polymer formation becomes pronounced, resulting in reduction in the yield of the reaction, and when the amount is more than 10% by mass, the yield may be significantly reduced. Further, specific examples of the ammonium salt include ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate and ammonium hydroxide. Ammonium nitrate, ammonium sulfate and ammonium chloride are more preferred, and ammonium nitrate is most preferred.

The method for producing the compound represented by formula (5) from the compound represented by formula (4) will be described below.

The compound represented by formula (5) can be obtained by reacting the compound represented by formula (4) with the epihalohydrin compound. Examples of the epihalohydrin compound include epichlorohydrin and epibromohydrin, and preferred is epichlorohydrin.

When reacting epihalohydrin with the compound represented by formula (4), a catalyst is preferably used. Examples of the catalyst include inorganic acids, organic acids, Lewis acids, silicic acid, boric acid, quaternary ammonium salts, inorganic bases and organic bases. Among them, organic acids, quaternary ammonium salts and inorganic bases are preferred, and quaternary ammonium salts and inorganic bases are more preferred. Specific examples thereof include tetramethylammonium chloride, tetramethylammonium bromide, tetramethylammonium acetate, tetraethylammonium chloride, tetraethylammonium bromide, tetraethylammonium acetate, tetrabutylammonium chloride, tetrabutylammonium bromide, tetrabutylammonium acetate, tetrahexylammonium chloride, tetrahexylammonium bromide, tetrahexylammonium acetate, tetraoctylammonium chloride, tetraoctylammonium bromide, tetraoctylammonium acetate, sodium hydroxide, potassium hydroxide, magnesium hydroxide and calcium hydroxide. Among them, sodium hydroxide, potassium hydroxide and calcium hydroxide are preferred.

The amount of the catalyst to be added is not particularly limited as long as it is for promoting a reaction, but is preferably 0.00001 to 0.5 mol, and more preferably 0.001 to 0.1 mol per 1 mol of epihalohydrin. When the amount is less than 0.00001 mol, the reaction does not proceed or is too slow, and it is undesirable. When the amount is more than 0.5 mol, the reaction proceeds excessively and is difficult to be controlled, and it is undesirable.

The ratio between epihalohydrin and the compound represented by formula (4) is not particularly limited as long as the reaction proceeds, but the molar ratio of epihalohydrin to the thiol group (SH group) of the compound represented by formula (4) is preferably 0.3 to 4, more preferably 0.4 to 3, and even more preferably 0.5 to 2. When the molar ratio is less than 0.3 or more than 4, the amount of unreacted raw materials increases, and it is undesirable from the economical viewpoint.

A solvent may be used but does not have to be used. In the case of using the solvent, water, alcohols, ethers, ketones, aromatic hydrocarbons, halogenated hydrocarbons, etc. can be used. Specific examples thereof include water, methanol, ethanol, propanol, isopropanol, diethyl ether, tetrahydrofuran, dioxane, methyl cellosolve, ethyl cellosolve, butyl cellosolve, methyl ethyl ketone, acetone, benzene, toluene, xylene, dichloroethane, chloroform and chlorobenzene. Among them, water, methanol and toluene are preferred, and water and methanol are particularly preferred.

The reaction temperature is not particularly limited as long as it is for promoting a reaction, but is preferably −10° C. to 80° C., more preferably 0° C. to 50° C., and even more preferably 0° C. to 40° C. The reaction time is not particularly limited, but is usually 20 hours or less. When the reaction temperature is lower than −10° C., the reaction does not proceed or is too slow, and it is undesirable. When the reaction temperature is higher than 80° C., oligomerization occurs, resulting in a high molecular weight, and it is undesirable.

The method for producing the compound represented by formula (6) from the compound represented by formula (5) will be described below. The compound represented by formula (7) can be produced from the compound represented by formula (3) in the same manner.

The compound represented by formula (6) can be obtained by reacting the compound represented by formula (5) with an alkali. Specific examples of the alkali include ammonia, hydroxides of alkali metals and alkaline earth metals, carbonates of alkali metals and alkaline earth metals, hydrogencarbonates of alkali metals, and ammonium salts of alkali metals and alkaline earth metals. These substances may be used in the form of an aqueous solution. Preferred are sodium hydroxide, potassium hydroxide, calcium hydroxide, sodium carbonate, potassium carbonate, ammonium carbonate, sodium hydrogen carbonate and potassium hydrogen carbonate, and more preferred are sodium hydroxide and potassium hydroxide.

The amount of the alkali to be used varies depending on the type of the compound represented by formula (5) as the raw material, but is usually 0.8 to 1.2 equivalents, preferably 0.84 to 1.14 equivalents, and more preferably 0.90 to 1.1 equivalents relative to the halogen equivalent in the compound represented by formula (5). When the amount of the alkali is smaller or larger, the yield is reduced.

Any solvent may be used during the reaction without particular limitation, but preferably, water, alcohols, ethers, ketones, aliphatic hydrocarbons, aromatic hydrocarbons, halogenated hydrocarbons, etc. are used. These substances may be used solely, or two or more of them may be used in combination. Specific examples of the alcohols include methanol, ethanol, propanol and isopropanol. Specific examples of the ethers include diethyl ether, tetrahydrofuran and dioxane. Specific examples of the ketones include methyl cellosolve, ethyl cellosolve, butyl cellosolve, methyl ethyl ketone and acetone. Specific examples of the aliphatic hydrocarbons include hexane, heptane and octane. Specific examples of the aromatic hydrocarbons include benzene, toluene and xylene. Specific examples of the halogenated hydrocarbons include dichloroethane, chloroform and chlorobenzene. More preferred are water and alcohols, and specific examples thereof include water, methanol, propanol and isopropanol. Among them, water and methanol are preferred.

The amount of the solvent is not particularly limited, but is usually 5 to 1000 parts by mass, preferably 50 to 500 parts by mass, and more preferably 100 to 300 parts by mass per 100 parts by mass of the compound represented by formula (3).

The reaction temperature is not particularly limited as long as it is for promoting a reaction, but is preferably −10° C. to 80° C., more preferably 0° C. to 50° C., and even more preferably 0° C. to 30° C. The reaction time is not particularly limited, but is usually 20 hours or less. When the reaction temperature is lower than −10° C., the reaction does not proceed or is too slow, and it is undesirable. When the reaction temperature is higher than 80° C., oligomerization occurs, resulting in a high molecular weight, and it is undesirable.

The method for producing the compound represented by formula (1), wherein n and q are 0, from the compound represented by formula (6) will be described below. The compound represented by formula (1) can be produced from the compound represented by formula (8) in the same manner.

The episulfide compound represented by formula (1) is obtained by reacting the compound represented by formula (6) with a thialation agent such as thiourea and a thiocyanate. Preferred thialation agents are thiourea, sodium thiocyanate, potassium thiocyanate and ammonium thiocyanate, and particularly preferred is thiourea. The thialation agent is used in a mole number corresponding to epoxy of the compound represented by formula (6), i.e., a theoretical amount, but when importance is placed on the reaction rate and the purity, the thialation agent is used in the theoretical amount to 2.5 times the theoretical amount (mol). The amount is preferably from 1.3 times the theoretical amount (mol) to 2.0 times the theoretical amount (mol), and more preferably from 1.5 times the theoretical amount (mol) to 2.0 times the theoretical amount (mol).

The solvent is not particularly limited as long as it dissolves the thialation agent, the compound represented by formula (6) and the episulfide compound represented by formula (1). Specific examples thereof include: alcohols such as methanol and ethanol; ethers such as diethyl ether, tetrahydrofuran and dioxane; hydroxy ethers such as methyl cellosolve, ethyl cellosolve and butyl cellosolve; aromatic hydrocarbons such as benzene and toluene; halogenated hydrocarbons such as dichloromethane, chloroform and chlorobenzene; and water. Preferred are alcohols, aromatic hydrocarbons and water, and more preferred are methanol and toluene. These substances may be used solely, or two or more of them may be used in combination.

The reaction temperature is not particularly limited as long as the reaction proceeds, but the reaction is usually performed at 10° C. to 50° C. When the reaction temperature is lower than 10° C., not only the reaction rate is reduced, but also the thialation agent is not sufficiently dissolved and the reaction does not proceed sufficiently, and when the temperature is higher than 50° C., polymer formation becomes pronounced.

It is preferred to add an acid, acid anhydride or ammonium salt at the time of the reaction. Specific examples of the acid or acid anhydride to be used include: inorganic acidic compounds such as nitric acid, hydrochloric acid, perchloric acid, hypochlorous acid, chlorine dioxide, hydrofluoric acid, sulfuric acid, fuming sulfuric acid, sulfuryl chloride, boric acid, arsenic acid, arsenious acid, pyroarsenic acid, phosphoric acid, phosphorous acid, hypophosphoric acid, phosphorus oxychloride, phosphorous oxybromide, phosphorus sulfide, phosphorus trichloride, phosphorus tribromide, phosphorus pentachloride, hydrocyanic acid, chromic acid, nitric anhydride, sulphuric anhydride, boron oxide, arsenic pentoxide, phosphorus pentoxide, chromic anhydride, silica gel, silica alumina, aluminium chloride and zinc chloride; organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid, acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride; phosphoric acids such as mono-, di- or trimethyl phosphate, mono-, di- or triethyl phosphate, mono-, di- or triisobutyl phosphate, mono-, di- or tributyl phosphate and mono-, di- or trilauryl phosphate, and phosphorous acids in which the phosphate moiety of any of the phosphoric acids is changed to a phosphite; organic phosphorous compounds such as dialkyl phosphorodithioates typified by dimethyl phosphorodithioate; phenols such as phenol, catechol, t-butyl catechol, 2,6-di-t-butyl cresol, 2,6-di-t-butyl ethylphenol, resorcin, hydroquinone, phloroglucin, pyrogallol, cresol, ethyl phenol, butyl phenol, nonyl phenol, hydroxyphenylacetic acid, hydroxyphenylpropionic acid, hydroxyphenylacetamide, methyl hydroxyphenylacetate, ethyl hydroxyphenylacetate, hydroxyphenethyl alcohol, hydroxyphenethyl amine, hydroxybenzaldehyde, phenylphenol, bisphenol A, 2,2'-methylene-bis(4-methyl-6-t-butyl phenol), bisphenol F, bisphenol S, α-naphthol, β-naphthol, aminophenol, chlorophenol and 2,4,6-trichlorophenol; and sulfonic acids such as methanesulfonic acid, ethanesulfonic acid, butanesulfonic acid, dodecanesulfonic acid, benzenesulfonic acid, o-toluenesulfonic acid, m-toluenesulfonic acid, p-toluenesulfonic acid, ethylbenzenesulfonic acid, butylbenzenesulfonic acid, dodecylbenzenesulfonic acid, p-phenolsulfonic acid, o-cresolsulfonic acid, metanilic acid, sulfanilic acid, 4B-acid, diaminostilbenesulfonic acid, biphenylsulfonic acid, α-naphthalenesulfonic acid, β-naphthalenesulfonic acid, peri acid, Laurent's acid and phenyl-J-acid. Several of them may be used in combination. Preferred are organic carboxylic acids such as formic acid, acetic acid, peracetic acid, thioacetic acid, oxalic acid, tartaric acid, propionic acid, butyric acid, succinic acid, valeric acid, caproic acid, caprylic acid, naphthenic acid, methyl mercaptopropionate, malonic acid, glutaric acid, adipic acid, cyclohexanecarboxylic acid, thiodipropionic acid, dithiodipropionic acid, acetic acid, maleic acid, benzoic acid, phenylacetic acid, o-toluic acid, m-toluic acid, p-toluic acid, salicylic acid, 2-methoxybenzoic acid, 3-methoxybenzoic acid, benzoylbenzoic acid, phthalic acid, isophthalic acid, terephthalic acid, salicylic acid, benzilic acid, α-naphthalenecarboxylic acid, β-naphthalenecarboxylic acid, acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. More preferred are acid anhydrides such as acetic anhydride, propionic anhydride, butyric anhydride, succinic anhydride, maleic anhydride, benzoic anhydride, phthalic anhydride, pyromellitic dianhydride, trimellitic anhydride and trifluoroacetic anhydride. Acetic anhydride is most preferred. The amount to be added is usually 0.001 to 10% by mass, and preferably 0.01 to 5% by mass relative to the total amount of the reaction solution. When the amount to be added is less than 0.001% by mass, polymer formation becomes pronounced, resulting in reduction in the yield of the reaction, and when the amount is more than 10% by mass, the yield may be significantly reduced. Further, specific examples of the ammonium salt include ammonium chloride, ammonium bromide, ammonium iodide, ammonium formate, ammonium acetate, ammonium propionate, ammonium benzoate, ammonium sulfate, ammonium nitrate, ammonium carbonate, ammonium phosphate and ammonium hydroxide. Ammonium nitrate, ammonium sulfate and ammonium chloride are more preferred, and ammonium nitrate is most preferred.

The method for producing the compound represented by formula (1), wherein m and p are 0 and n and q are 1, from the compound represented by formula (4) will be described below.

The episulfide compound represented by formula (1) is obtained by reacting the compound represented by formula (4) with 3-mercapto-1,2-propylenesulfide using an oxidant. Preferred oxidants are halogen, hydrogen peroxide, permanganate and chromic acid. More preferred are halogen and hydrogen peroxide, and particularly preferred is iodine.

The solvent is not particularly limited as long as it dissolves the oxidant, the compound represented by formula (4) and the episulfide compound represented by formula (1). Specific examples thereof include: alcohols such as methanol and ethanol; ethers such as diethyl ether, tetrahydrofuran and dioxane; hydroxy ethers such as methyl cellosolve, ethyl cellosolve and butyl cellosolve; aromatic hydrocarbons such as benzene and toluene; halogenated hydrocarbons such as dichloromethane, chloroform and chlorobenzene; and water. Preferred are alcohols, aromatic hydrocarbons and water, and more preferred are methanol and toluene. These substances may be used solely, or two or more of them may be used in combination.

The reaction temperature is not particularly limited as long as the reaction proceeds, but the reaction is usually performed at −30° C. to 20° C. When the reaction temperature is lower than −30° C., the reaction rate is reduced, and for this reason, the reaction does not proceed sufficiently. When the temperature is higher than 20° C., the reaction may proceed excessively.

In the composition for optical materials of the present invention, it is possible to use an episulfide compound represented by formula (2) above as a polymerizable compound. Specific examples of the episulfide compound represented by formula (2) include episulfides such as bis(β-epithiopropyl)sulfide, bis(β-epithiopropyl)disulfide, bis(β-epithiopropylthio)methane, 1,2-bis(β-epithiopropylthio)ethane, 1,3-bis(β-epithiopropylthio)propane and 1,4-bis(β-epithiopropylthio)butane. As the episulfide compound represented by formula (2), such compounds may be used solely, or two or more compounds may be used in combination.

Among the above-described compounds, bis(β-epithiopropyl)sulfide (n=0 in formula (2)) and bis(β-epithiopropyl)disulfide (m=0 and n=1 in formula (2)) are preferred, and bis(β-epithiopropyl)sulfide (n=0 in formula (2)) is most preferred.

The composition for optical materials of the present invention may include a polythiol compound as a polymerizable compound for improving the color tone of obtained resin at the time of heating. The content of the polythiol compound is usually 1 to 25% by mass, preferably 2 to 25% by mass, and particularly preferably 5 to 20% by mass when the total amount of the composition for optical materials is 100% by mass. When the content of the polythiol compound is less than 1% by mass, yellowing may occur at the time of lens molding, and when the content is more than 25% by mass, the heat resistance may be reduced. As the polythiol compound to be used in the present invention, compounds may be used solely, or two or more of them may be used in combination.

Specific examples thereof include methanedithiol, methanetrithiol, 1,2-dimercaptoethane, 1,2-dimercaptopropane, 1,3-dimercaptopropane, 2,2-dimercaptopropane, 1,4-dimercaptobutane, 1,6-dimercaptohexane, bis(2-mercaptoethyl)ether, bis(2-mercaptoethyl)sulfide, 1,2-bis(2-mercaptoethyloxy)ethane, 1,2-bis(2-mercaptoethylthio)ethane, 2,3-dimercapto-1-propanol, 1,3-dimercapto-2-propanol, 1,2,3-trimercaptopropane, 2-mercaptomethyl-1,3-dimercaptopropane, 2-mercaptomethyl-1,4-dimercaptobutane, 2-(2-mercaptoethylthio)-1,3-dimercaptopropane, 4-mercaptomethyl-1,8-dimercapto-3,6-dithiaoctane, 2,4-dimercaptomethyl-1,5-dimercapto-3-thiapentane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,1-tris(mercaptomethyl)propane, tetrakis(mercaptomethyl)methane, ethyleneglycol bis(2-mercaptoacetate), ethyleneglycol bis(3-mercaptopropionate), diethyleneglycol bis(2-mercaptoacetate), diethyleneglycol bis(3-mercaptopropionate), 1,4-butanediol bis(2-mercaptoacetate), 1,4-butanediol bis(3-mercaptopropionate), trimethylolpropane tris(thioglycolate), trimethylolpropane tris(mercapto propionate), pentaerythritol tetrakis-thioglycolate, pentaerythritol tetrakis-mercaptopropionate, 1,2-dimercaptocyclohexane, 1,3-dimercaptocyclohexane, 1,4-dimercaptocyclohexane, 1,3-bis(mercaptomethyl)cyclohexane, 1,4-bis(mercaptomethyl)cyclohexane, 2,5-dimercaptomethyl-1,4-dithiane, 2,5-dimercaptomethyl-1,4-dithiane, 2,5-bis(2-mercaptoethylthiomethyl)-1,4-dithiane, 2,5-dimercaptomethyl-1-thiane, 2,5-dimercaptoethyl-1-thiane, 2,5-dimercaptomethylthiophene, 1,2-dimercaptobenzene, 1,3-dimercaptobenenne, 1,4-dimercaptobenzene, 1,3-bis(mercaptomethyl)benzene, 1,4-bis(mercaptomethyl)benzene, 2,2'-dimercaptobiphenyl, 4,4'-dimercaptobiphenyl, bis(4-mercaptophenyl)methane, 2,2-bis(4-mercaptophenyl)propane, bis(4-mercaptophenyl)ether, bis(4-mercaptophenyl)sulfide, bis(4-mercaptophenyl)sulfone, bis(4-mercaptomethylphenyl)methane, 2,2-bis(4-mercaptomethylphenyl)propane, bis(4-mercaptomethylphenyl)ether, bis(4-mercaptomethylphenyl)sulfide, 2,5-dimercapto-1,3,4-thiadiazole, 3,4-thiophenedithiol and 1,1,3,3-tetrakis(mercaptomethylthio)propane.

Among them, bis(2-mercaptoethyl)sulfide, 2,5-dimercaptomethyl-1,4-dithiane, 1,3-bis(mercaptomethyl)benzene, 1,4-bis(mercaptomethyl)benzene, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 1,1,3,3-tetrakis(mercaptomethylthio)propane, pentaerythritol tetrakis-mercaptopropionate, pentaerythritol tetrakis-thioglycolate, trimethylolpropane tris(thioglycolate) and trimethylolpropane tris(mercapto propionate) are preferred, bis(2-mercaptoethyl)sulfide, 2,5-bis(2-mercaptomethyl)-1,4-dithiane, 4-mercaptomethyl-1,8-dimercapto-3,6-dithiaoctane, 1,3-bis(mercaptomethyl)benzene, pentaerythritol tetrakis-mercaptopropionate and pentaerythritol tetrakis-thioglycolate are more preferred, and bis(2-mercaptoethyl) sulfide, 2,5-dimercaptomethyl-1,4-dithiane and 4-mercaptomethyl-1,8-dimercapto-3,6-dithiaoctane are particularly preferred.

The composition for optical materials of the present invention may include a polyisocyanate compound as a polymerizable compound for improving the strength of obtained resin. The content of the polyisocyanate compound is usually 1 to 25% by mass, preferably 2 to 25% by mass, and particularly preferably 5 to 20% by mass when the total amount of the composition for optical materials is 100% by mass. When the content of the polyisocyanate compound is less than 1% by mass, the strength may be reduced, and when the content is more than 25% by mass, the color tone may be deteriorated. As the polyisocyanate compound to be used in the present invention, compounds may be used solely, or two or more of them may be used in combination.

Specific examples thereof include diethylene diisocyanate, tetramethylene diisocyanate, hexamethylene diisocyanate, trimethylhexamethylene diisocyanate, cyclohexane diisocyanate, 1,3-bis(isocyanatemethyl)cyclohexane, 1,4-bis(isocyanatemethyl)cyclohexane, isophorone diisocyanate, 2,6-bis(isocyanatemethyl)decahydronaphthalene, lysine triisocyanate, tolylene diisocyanate, o-tolidine diisocyanate, diphenylmethane diisocyanate, diphenylether diisocyanate, 3-(2'-isocyanatecyclohexyl)propylisocyanate, isopropylidene bis(cyclohexyl isocyanate), 2,2'-bis(4-isocyanatephenyl)propane, triphenylmethane triisocyanate, bis(diisocyanatetolyl)phenylmethane, 4,4',4"-triisocyanate-2,5-dimethoxyphenylamine, 3,3'-dimethoxybenzidine-4,4'-diisocyanate, 1,3-phenylene diisocyanate, 1,4-phenyiene diisocyanate, 4,4'-diisocyanatebiphenyl, 4,4'-diisocyanate-3,3'-dimethylbiphenyl, dicyclohexylmethane-4,4'-diisocyanate, 1,1'-methylenebis(4-isocyanatebenzene), 1,1'-methylenebis(3-methyl-4-isocyanatebenzene), m-xylylene diisocyanate, p-xylylene diisocyanate, m-tetramethyl xylylene diisocyanate, p-tetramethyl xylylene diisocyanate, 1,3-bis(2-isocyanate-2-propyl)benzene, 2,6-bis(isocyanatemethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)norbornene, bis(isocyanatemethyl)adamantane, thiodiethyl diisocyanate, thiodipropyl diisocyanate, thiodihexyl diisocyanate, bis[(4-isocyanatemethyl)phenyl]sulfide, 2,5-diisocyanate-1,4-dithiane, 2,5-diisocyanatemethyl-1,4-dithiane, 2,5-diisocyanatemethylthiophene, dithiodiethyl diisocyanate and dithiodipropyl diisocyanate.

However, the polyisocyanate compound to be used in the present invention is not limited thereto, and these substances may be used solely, or two or more of them may be used in combination.

Among them, isophorone diisocyanate, tolylene diisocyanate, diphenylmethane diisocyanate, hexamethylene diisocyanate, m-xylylene diisocyanate, p-xylylene diisocyanate, m-tetramethyl xylylene diisocyanate, p-tetramethyl xylylene diisocyanate, 1,3-bis(isocyanatemethyl)cyclohexane, 1,4-bis(isocyanatemethyl)cyclohexane, bis(isocyanatemethyl)norbomene and 2,5-diisocyanatemethyl-1,4-dithiane are preferred. Among them, isophorone diisocyanate, tolylene diisocyanate, diphenylmethane diisocyanate, hexamethylene diisocyanate, 1,3-bis(isocyanatemethyl)cyclohexane and m-xylylene diisocyanate are preferred, and isophorone diisocyanate, m-xylylene diisocyanate and 1,3-bis(isocyanatemethyl)cyclohexane are particularly preferred.

Further, the ratio of the SH groups in the polythiol compound to the NCO groups in the polyisocyanate compound, i.e., [the number of the SH groups in the polythiol compound/the number of the NCO groups in the polyisocyanate compound](SH group/NCO group) is preferably 1.0 to 2.5, more preferably 1.25 to 2.25, and even more preferably 1.5 to 2.0. When the above-described ratio is less than 1.0, yellowing may occur at the time of lens molding, and when the ratio is more than 2.5, the heat resistance may be reduced.

The composition for optical materials of the present invention may include sulfur as a polymerizable compound for improving the refractive index of obtained resin. The content of sulfur is usually 0.1 to 15% by mass, preferably 0.2 to 10% by mass, and particularly preferably 0.3 to 5% by mass when the total amount of the composition for optical materials is 100% by mass. Further, in the method for producing an optical material of the present invention, it is possible to partially subjecting the compound represented by formula (2) and sulfur to a polymerization reaction in advance.

The sulfur to be used in the present invention may be in any form. Specifically, the sulfur is finely-powdered sulfur, colloidal sulfur, precipitated sulfur, crystalline sulfur, sublimed sulfur or the like, and is preferably finely-powdered sulfur having fine particles.

The sulfur to be used in the present invention may be produced by any production method. Examples of methods for producing sulfur include methods of sublimation and purification from natural sulfur ores, methods of mining underground sulfur by means of the melting method, and methods of recovery using, for example, hydrogen sulfide obtained in the process of desulfurization of petroleum oil, natural gas or the like, as a raw material, but any of these production methods may be employed.

It is preferred that the particle size of the sulfur to be used in the present invention is less than 10 mesh, that is, the sulfur is in the form of fine powder having a particle size of less than 10 mesh. When the particle size of the sulfur is more than 10 mesh, it is difficult to dissolve the sulfur completely. For this reason, an undesirable reaction or the like may be caused in the first step to generate a defect. The particle size of the sulfur is more preferably less than 30 mesh, and most preferably less than 60 mesh.

The purity of the sulfur to be used in the present invention is preferably at least 98%, more preferably at least 99.0%, even more preferably at least 99.5%, and most preferably at least 99.9%. When the purity of the sulfur is at least 98%, the color tone of the obtained optical material is improved compared to the case of lower than 98%.

When obtaining an optical material by polymerizing and curing the composition for optical materials of the present invention, it is preferred to add a polymerization catalyst. The composition of the present invention may be a polymerizable and curable composition containing a composition for optical materials and a polymerization catalyst. As the polymerization catalyst, amines, phosphines, onium salts, etc. may be used, but onium salts are particularly preferred. Among them, quaternary ammonium salts, quaternary phosphonium salts, tertiary sulfonium salts and secondary iodonium salts are preferred. Among them, quaternary ammonium salts and quaternary phosphonium salts, which have good compatibility with the composition for optical materials, are even more preferred, and quaternary phosphonium salts are even more preferred. More preferred examples of the polymerization catalyst include quaternary ammonium salts such as tetra-n-butylammonium bromide, triethylbenzyl ammonium chloride, cetyldimethylbenzyl ammonium chloride and 1-n-dodecyl pyridinium chloride and quaternary phosphonium salts such as tetra-n-butylphosphonium bromide and tetraphenyl phosphonium bromide. Among them, tetra-n-butylammonium bromide, triethylbenzyl ammonium chloride and tetra-n-butylphosphonium bromide are even more preferred polymerization catalysts.

The amount of the polymerization catalyst to be added cannot be determined categorically because it varies depending on the components of the composition, the mixing ratio and the method for polymerization and curing, but the amount is usually 0.0001% by mass to 10% by mass, preferably 0.001% by mass to 5% by mass, more preferably 0.01% by mass to 1% by mass, and most preferably 0.01% by mass to 0.5% by mass when the total amount of the composition for optical materials is 100% by mass (amount not including the polymerization catalyst). When the amount of the polymerization catalyst to be added is more than 10% by mass, the composition may be rapidly polymerized. When the amount of the polymerization catalyst to be added is less than 0.0001% by mass, the composition for optical materials may be insufficiently cured, resulting in poor heat resistance.

Moreover, in the production of the optical material according to the production method of the present invention, it is surely possible to add additives such as an ultraviolet absorber, a blueing agent and a pigment to the composition for optical materials to further improve practicability of the optical material obtained.

Preferred examples of the ultraviolet absorber include benzotriazole-based compounds, and 2-(2-hydroxy-5-methylphenyl)-2H-benzotriazol, 5-chloro-2-(3,5-di-tert-butyl-2-hydroxyphenyl)-2H-benzotriazol, 2-(2-hydroxy-4-octylphenyl)-2H-benzotriazol, 2-(2-hydroxy-4-methoxyphenyl)-2H-benzotriazol, 2-(2-hydroxy-4-ethoxyphenyl)-2H-benzotriazol, 2-(2-hydroxy-4-butoxyphenyl)-2H-benzotriazol, 2-(2-hydroxy-4-octyloxyphenyl)-2H-benzotriazol and 2-(2-hydroxy-5-t-octylphenyl)-2H-benzotriazol are particularly preferred compounds.

The amount of each of such ultraviolet absorbers to be added is usually 0.01 to 5% by mass when the total amount of the composition for optical materials is 100% by mass.

When polymerizing and curing the composition for optical materials, for the purpose of extension of the pot life, dispersion of heat generated by polymerization, etc., a polymerization modifier may be added according to need. Examples of the polymerization modifier include halides of groups 13 to 16 of the long form of the periodic table. Among them, halides of silicon, germanium, tin and antimony are preferred, and chlorides of germanium, tin and antimony, which have an alkyl group, are more preferred. Further, dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium and triphenylantimony dichloride are even more preferred, and dibutyltin dichloride is the most preferred compound. These polymerization modifiers may be used solely, or two or more of them may be used in combination.

The amount of the polymerization modifier to be added is 0.0001 to 5.0% by mass, preferably 0.0005 to 3.0% by mass, and more preferably 0.001 to 2.0% by mass when the total amount of the composition for optical materials is 100% by mass. When the amount of the polymerization modifier to be added is less than 0.0001% by mass, sufficient pot life cannot be ensured in the obtained optical material, and when the amount of the polymerization modifier to be added is more than 5.0% by mass, the composition for optical materials may not be sufficiently cured, and the heat resistance of the obtained optical material may be reduced.

The composition for optical materials or polymerizable and curable composition thus obtained is injected into a mold or the like and polymerized to obtain an optical material.

At the time of cast-molding the composition of the present invention, it is preferred to filter and remove impurities using, for example, a filter having a pore diameter of about 0.1 to 5 μm in terms of improving the quality of the optical material of the present invention.

The composition of the present invention is usually polymerized as described below. Specifically, the curing time is usually 1 to 100 hours, and the curing temperature is usually −10° C. to 140° C. The polymerization is conducted by carrying out a step of retaining the composition at a predetermined polymerization temperature for a predetermined amount of time, a step of increasing the temperature at a rate of 0.1° C. to 100° C./h and a step of decreasing the temperature at a rate of 0.1° C. to 100° C./h, or a combination of these steps.

Further, it is preferred to anneal the obtained optical material at a temperature of 50 to 150° C. for about 10 minutes to 5 hours after curing is completed in terms of eliminating distortion of the optical material of the present invention. Moreover, the obtained optical material may be subjected to a surface treatment such as dyeing, hard coating, impact-resistant coating, antireflection treatment and imparting antifog properties according to need.

The optical material of the present invention can be suitably used as an optical lens. An optical lens produced by using the composition of the present invention is excellent in stability, color phase, light resistance and transparency, and therefore can be used in the field in which expensive glass lenses having a high refractive index have been conventionally used including telescopes, binoculars and television projectors and is very useful. The optical lens is preferably used in the form of an aspherical lens according to need. In the case of the aspherical lens, since the spherical aberration can be adjusted to be substantially zero by one lens, it is not necessary to remove the spherical aberration by combining a plurality of spherical lenses, and reduction in weight and reduction in the production cost can be carried out. Accordingly, the aspherical lens is particularly useful as a camera lens among optical lenses.

EXAMPLES

Hereinafter, the present invention will be specifically described by way of working examples and comparative examples. However, the present invention is not limited to the below-described working examples.
1. Method for Evaluating Dyeability The optical material was immersed in a dye bath having the below-described composition at 90° C. for 30 minutes, and then the total light transmittance was measured. The value obtained by calculation with the measurement value according to the below-described formula was regarded as dyeability.

Dyeability=100−total light transmittance (%)

Dye Bath Composition:
Seiko Purakkusu Dia-coat Blown D: 0.2% by weight
Seiko Purakkusu dyeing auxiliary: 0.3% by weight
Benzyl alcohol: 2.0% by weight The case where the dyeability is 70 or more was rated as "A". The case where the dyeability is 55 or more and less than 70 was rated as "B". The case where the dyeability is 40 or more and less than 55 was rated as "C". The case where the dyeability is less than 40 was rated as "D". A, B and C are regarded as acceptable.
2. Method for Evaluating Mold Release Characteristics 100 lenses having a lens power of −10D were prepared according to the method described in the Examples, and mold release characteristics after polymerization and curing were evaluated. The case where no lens was broken was rated as "A". The case where 1 to 2 lenses were broken was rated as "B". The case where 3 or more lenses were broken was rated as "C". A and B are regarded as acceptable.
3. Method for Evaluating Peeling Traces 100 lenses having a lens power of −10D were prepared according to the method described in the Examples. Each lens after polymerization and curing was observed using a mercury lamp, and peeling traces were evaluated based on the number of lenses with poor surface accuracy generated. The case where no peeling trace was generated in the lenses was rated as "A". The case where 1 to 2 lenses had peeling traces was rated as "B". The case where 3 or more lenses had peeling traces was rated as "C". A and B are regarded as acceptable.

Synthesis Example 185 g (2.0 mol) of epichlorohydrin, 30 g of water, 5 g of methanol and 1.5 g of 32% aqueous solution of sodium hydroxide were put into a 3 L flask, and 35 g (1.0 mol) of hydrogen sulfide was blown into the flask while the mixture was stirred with the temperature of the solution being maintained at 5 to 15° C., thereby obtaining 210 g (0.96 mol) of bis(3-chloro-2-hydroxypropyl)sulfide.

After that, 750 ml of toluene, 750 ml of methanol, 0.3 g of acetic anhydride and 350 g of thiourea were added thereto, and the reaction was performed at 40° C. for 10 hours. After the reaction was completed, water was added thereto to carry out washing, the obtained organic layer was washed with 10% sulfuric acid and then washed with water, the solvent was distilled away, and then purification was carried out in a column, thereby obtaining 139 g (0.65 mol) of 1,7-dimercapto-2,6-dihydroxy-4-thiaheptane.

Example 1

19.5 g (0.2 mol) of epichlorohydrin, 30 g of water, 5 g of methanol and 0.2 g of 32% aqueous solution of sodium hydroxide were put into a 1 L flask, and 21.4 g (0.1 mol) of 1,7-dimercapto-2,6-dihydroxy-4-thiaheptane obtained in the above-described Synthesis Example was added dropwise thereto while the mixture was stirred with the temperature of the solution being maintained at 5 to 15° C., thereby obtaining bis-(2,6-dihydroxy-7-chloro-4-thiaheptyl)sulfide.

100 g of water was added thereto, and then 25 g of 32% aqueous solution of sodium hydroxide was added dropwise thereto with the temperature being maintained at 0 to 10° C. After that, 100 g of methyl isobutyl ketone was added thereto to carry out extraction, the obtained organic layer was washed with 1% acetic acid and then washed with water, the solvent was distilled away, and then purification was carried out in a column, thereby obtaining 20 g (0.06 mol) of bis-(2-hydroxy-6,7-epoxy-4-thiaheptyl)sulfide.

After that, 200 ml of toluene, 200 ml of methanol, 0.2 g of acetic anhydride and 19 g of thiourea were added thereto, and the reaction was performed at 40° C. for 10 hours. After the reaction was completed, water was added thereto to carry out washing, the obtained organic layer was washed with 10% sulfuric acid and then washed with water, the solvent was distilled away, and then purification was carried out in a column, thereby obtaining 16 g (0.04 mol) of bis-(2-hydroxy-6,7-epithio-4-thiaheptyl)sulfide represented by the below-described structural formula:

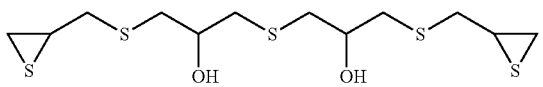 [SMILES: OC(CSCC(O)CSCC1CS1)CSCC1CS1]

$^1$H-NMR (CDCl$_3$): 2.0 ppm (2H), 2.2-2.7 ppm (18H), 3.8 ppm (2H)
$^{13}$C-NMR (CDCl$_3$): 26 ppm (2C), 33 ppm (4C), 44 ppm (2C), 45 ppm (2C), 77 ppm (2C)

Example 2

15 g (0.07 mol) of 1,7-dimercapto-2,6-dihydroxy-4-thiaheptane obtained in the Synthesis Example, 15 g (0.14 mol) of 3-mercapto-1,2-propylenesulfide, 100 mL of toluene, 100 mL of methanol and 23.2 g (0.14 mol) of potassium iodide were put into a 1 L flask. The mixture was stirred with the internal temperature being maintained at −20° C., and 35.6 g (0.14 mol) of solid iodine was fed portionwise thereto to carry out maturation for 4 hours. After the reaction was completed, 100 mL of toluene was added thereto, the organic layer was taken out and filtration was carried out, followed by washing with saline, 1% sulfuric acid, and then saline. The obtained organic layer was dehydrated with anhydrous magnesium sulfate and then filtered, and the solvent in the obtained filtrate was distilled away. After that, purification was carried out in a column, thereby obtaining 11.4 g (0.03 mol) of bis-(2-hydroxy-7,8-epithio-4,5-dithiaoctyl)sulfide represented by the below-described structural formula:

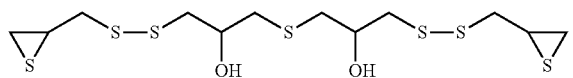 [SMILES: OC(CSCC(O)CSSCC1CS1)CSSCC1CS1]

$^1$H-NMR (CDCl$_3$): 2.0 ppm (2H), 2.2-3.0 ppm (18H), 3.8 ppm (2H)
$^{13}$C-NMR (CDCl$_3$): 24 ppm (2C), 33 ppm (4C), 45 ppm (2C), 46 ppm (2C), 78 ppm (2C)

Example 3

To bis(β-epithiopropyl)sulfide (hereinafter referred to as "the compound b-1") as the above-described episulfide compound represented by formula (2), bis-(2-hydroxy-6,7-epithio-4-thiaheptyl)sulfide obtained in Example 1 (hereinafter referred to as "the compound a-1") as the above-described episulfide compound represented by formula (1) was added to obtain a composition containing 0.001% by mass of the compound a-1. 79.0 parts by mass of the obtained composition, 0.5 parts by mass of sulfur and 0.9 parts by mass of 2,2-methylenebis[4-(1,1,3,3-tetramethylbutyl)-6-(2H-benzotriazol-2-yl)phenol] as the ultraviolet absorber (manufactured by Kyodo Chemical Co., Ltd., trade name: Biosorb 583) were mixed together homogenously at 30° C. for 1 hour, thereby obtaining a first solution. After that, the first solution was cooled to 10° C. 6.6 parts by mass of pentaerythritol tetrakis-mercaptopropionate, 0.08 parts by mass of tetra-n-butylphosphonium bromide and 0.01 parts by mass of dibutyltin dichloride were well mixed homogeneously at a mixing temperature of 20° C., and after that, the obtained mixture was added to the first solution and stirred homogenously at a mixing temperature of 15° C. for 30 minutes to obtain a second solution. 0.01 parts by mass of Zelec UN (manufactured by Stepan) as a mold release agent and 7.1 parts by mass of m-xylylene diisocyanate were well mixed homogeneously at 20° C., and then added to the second solution. The obtained mixture was subjected to the deaeration treatment and stirring at a reaction temperature of 15° C. at a vacuum degree of 0.27 kPa for 2.5 hours to react the mixture, thereby obtaining a reaction mixture. 6.8 parts by mass of bis(2-mercaptoethyl)sulfide was added to the reaction mixture in a reaction flask, and it was subjected to the deaeration treatment and stirring at 15° C. for 30 minutes at a vacuum degree of 0.27 kPa, thereby obtaining a composition for optical materials. The obtained composition for optical materials was injected into a mold composed of two glass plates and a tape, and it was retained at 30° C. for 30 hours, then the temperature was elevated to 100° C. over 10 hours, and finally, the composition was retained at 100° C. for 1 hour to be polymerized and cured. After cooling, the obtained product was released from the mold and annealed at 110° C. for 60 minutes. The evaluation results regarding mold release characteristics, peeling traces and dyeability are shown in Table 1.

Examples 4-9, Comparative Example 1

An optical material was obtained in a manner similar to that in Example 3, except that the amount of the compound a-1 (compound of formula (1)) to be added was changed. The evaluation results are shown in Table 1.

Example 10

To bis(β-epithiopropyl)disulfide (hereinafter referred to as "the compound b-2") as the above-described episulfide compound represented by formula (2), bis-(2-hydroxy-7,8-epithio-4,5-dithiaoctyl)sulfide obtained in Example 2 (hereinafter referred to as "the compound a-2") as the above-described episulfide compound represented by formula (1) was added to obtain a composition containing 0.001% by mass of the compound a-2. 79.0 parts by mass of the obtained composition, 0.5 parts by mass of sulfur and 0.9 parts by mass of 2,2-methylenebis[4-(1,1,3,3-tetramethylbutyl)-6-(2H-benzotriazol-2-yl)phenol] as the ultraviolet absorber (manufactured by Kyodo Chemical Co., Ltd., trade name: Biosorb 583) were mixed together homogenously at 30° C. for 1 hour, thereby obtaining a first solution. After that, the first solution was cooled to 10° C. 6.6 parts by mass of pentaerythritol tetrakis-mercaptopropionate, 0.08 parts by mass of tetra-n-butylphosphonium bromide and 0.01 parts by mass of dibutyltin dichloride were well mixed homogeneously at a mixing temperature of 20° C., and after that, the obtained mixture was added to the first solution and stirred homogenously at a mixing temperature of 15° C. for 30 minutes to obtain a second solution. 0.01 parts by mass of Zelec UN (manufactured by Stepan) as a mold release agent and 7.1 parts by mass of m-xylylene diisocyanate were well mixed homogeneously at 20° C., and then added to the second solution. The obtained mixture was subjected to the deaeration treatment and stirring at a reaction temperature of 15° C. at a vacuum degree of 0.27 kPa for 2.5 hours to react the mixture, thereby obtaining a reaction mixture. 6.8 parts by mass of bis(2-mercaptoethyl)sulfide was added to the reaction mixture in a reaction flask, and it was subjected to the deaeration treatment and stirring at 15° C. for 30 minutes at a vacuum degree of 0.27 kPa, thereby obtaining a composition for optical materials. The obtained composition for optical materials was injected into a mold composed of two glass plates and a tape, and it was retained at 30° C. for 30 hours, then the temperature was elevated to 100° C. over 10 hours, and finally, the composition was retained at 100° C. for 1 hour to be polymerized and cured. After cooling, the obtained product was released from the mold and annealed at 110° C. for 60 minutes. The evaluation results regarding mold release characteristics, peeling traces and dyeability are shown in Table 1.

Examples 11-16, Comparative Example 2

An optical material was obtained in a manner similar to that in Example 10, except that the amount of the compound a-2 (compound of formula (1)) to be added was changed. The evaluation results are shown in Table 1.

TABLE 1

| | Main component | Added component (adding amount) | Peeling traces | Mold release characteristics | Dyeability |
|---|---|---|---|---|---|
| Example 3 | b-1 | a-1 (0.001% by mass) | B | A | C |
| Example 4 | b-1 | a-1 (0.005% by mass) | B | A | B |
| Example 5 | b-1 | a-1 (0.01% by mass) | A | A | A |
| Example 6 | b-1 | a-1 (1% by mass) | A | A | A |
| Example 7 | b-1 | a-1 (3% by mass) | A | B | A |
| Example 8 | b-1 | a-1 (5% by mass) | A | B | A |
| Example 9 | b-1 | a-1 (10% by mass) | A | C | A |
| Comparative Example 1 | b-1 | None | C | A | D |
| Example 10 | b-2 | a-2 (0.001% by mass) | B | A | C |
| Example 11 | b-2 | a-2 (0.005% by mass) | B | A | B |
| Example 12 | b-2 | a-2 (0.01% by mass) | A | A | A |
| Example 13 | b-2 | a-2 (1% by mass) | A | A | A |
| Example 14 | b-2 | a-2 (3% by mass) | A | A | A |
| Example 15 | b-2 | a-2 (5% by mass) | A | B | A |
| Example 16 | b-2 | a-1 (10% by mass) | A | C | A |
| Comparative Example 2 | b-2 | None | C | A | D |

As understood from Table 1, in Examples 3-8 and 10-15, all of peeling traces, mold release characteristics and dyeability were evaluated as acceptable. Meanwhile, in Examples 9 and 16, peeling traces and dyeability were evaluated as good, but mold release characteristics were evaluated as bad. In Comparative Examples 1 and 2, in which the episulfide compound represented by formula (1) was not contained, mold release characteristics were evaluated as good, but peeling traces and dyeability were evaluated as bad.

The invention claimed is:

1. An episulfide compound represented by formula (1):

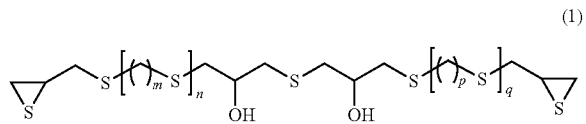

wherein m and p are each an integer between 0 and 4 and n and q are each an integer between 0 and 2.

2. A composition for optical materials, which comprises the episulfide compound represented by formula (1) according to claim 1 and an episulfide compound represented by formula (2):

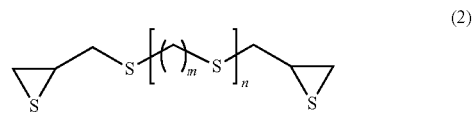

wherein m is an integer between 0 and 4 and n is an integer between 0 and 2.

3. The composition for optical materials according to claim 2, wherein the content of the episulfide compound represented by formula (1) is 0.001 to 5.0% by mass, relative to the total amount of the composition for optical materials.

4. The composition for optical materials according to claim 2, wherein the content of the episulfide compound represented by formula (2) is 40 to 99.999% by mass, relative to the total amount of the composition for optical materials.

5. The composition for optical materials according to claim 2, further comprising polythiol.

6. The composition for optical materials according to claim 5, further comprising polyisocyanate.

7. The composition for optical materials according to claim 2, further comprising sulfur.

8. A polymerizable and curable composition, which comprises the composition for optical materials according to claim 2 and a polymerization catalyst in an amount of 0.0001 to 10% by mass relative to the total amount of the composition for optical materials.

9. An optical material obtained by curing the polymerizable and curable composition according to claim 8.

10. An optical material obtained by curing the composition for optical materials according to claim 2.

11. An optical lens comprising the optical material according to claim 10.

12. A method for producing an optical material, which comprises adding a polymerization catalyst in an amount of 0.0001 to 10% by mass relative to the total amount of the composition for optical materials according to claim 2 to be polymerized and cured.

* * * * *